(12) United States Patent
Schwartz et al.

(10) Patent No.: US 10,751,067 B2
(45) Date of Patent: Aug. 25, 2020

(54) SELF-STABILIZING PORTABLE PNEUMATIC ABDOMINAL AORTIC TOURNIQUET WITH RATCHETING TENSIONER

(71) Applicant: Compression Works, LLC, Montgomery, AL (US)

(72) Inventors: Richard Schwartz, Evans, GA (US); John M Croushorn, Hoover, AL (US)

(73) Assignee: Compression Works, LLC, Birmingham, AL (US)

( * ) Notice: Subject to any disclaimer, the term of this patent is extended or adjusted under 35 U.S.C. 154(b) by 0 days.

(21) Appl. No.: 16/214,085

(22) Filed: Dec. 9, 2018

(65) Prior Publication Data

US 2020/0178984 A1 Jun. 11, 2020

(51) Int. Cl.
*A61B 17/132* (2006.01)
*A61B 17/135* (2006.01)
*A61B 17/00* (2006.01)

(52) U.S. Cl.
CPC ........ *A61B 17/1325* (2013.01); *A61B 17/135* (2013.01); *A61B 17/1327* (2013.01); *A61B 2017/00544* (2013.01)

(58) Field of Classification Search
CPC . A61B 17/132; A61B 17/1325; A61B 17/135; A61B 17/1322

USPC .......................................................... 606/203
See application file for complete search history.

(56) References Cited

U.S. PATENT DOCUMENTS

| | | |
|---|---|---|
| 5,201,758 A | 4/1993 | Glover |
| 7,947,061 B1 | 5/2011 | Reis |
| 2013/0310872 A1* | 11/2013 | Croushorn ......... A61B 17/1325 606/202 |
| 2015/0032149 A1 | 1/2015 | Croushorn et al. |
| 2018/0228495 A1 | 8/2018 | Carmichael et al. |

* cited by examiner

*Primary Examiner* — Diane D Yabut
*Assistant Examiner* — Majid Jamialahmadi
(74) *Attorney, Agent, or Firm* — The Gache Law Firm, P.C.; Russell C. Gache (57) ABSTRACT

A self-stabilizing pneumatic abdominal aortic tourniquet that utilizes a semi-ridge retaining strap, a ratcheting retaining buckle, and an elastic guide cord on the lower penetrating end of a wedge-shaped bladder. A rigid baseplate is supported by a waist belt having a width identical with the waist belt so that the baseplate provides a stable base for positioning the bladder over a selected area of the patient's abdomen. The air bladder is affixed to the underside of the baseplate, which is initially kept in a deflated condition collapsed against the baseplate, and includes an elastic cord, such as a shock cord, configured to bias the tip of the wedge or "V" shaped bladder in the middle of the baseplate. An air source connected to the air bladder causes inflation and penetration of the lower edge of the bladder into the patient's abdomen thereby causing aorta occlusion.

20 Claims, 10 Drawing Sheets

SELF-STABILIZING PORTABLE PNEUMATIC ABDOMINAL AORTIC TOURNIQUET WITH RATCHETING TENSIONER

FIELD OF THE INVENTION

The present invention relates generally to tourniquets. In greater particularity, the present invention relates to field dressings that utilize mechanical pressure to achieve homeostasis at the site of an injury. In even greater particularity, the present invention relates to strap-on tourniquets positioned to apply pressure on the body to stop bleeding.

BACKGROUND OF THE INVENTION

Various tourniquet devices that use a wide variety of clamping and/or pneumatic means to apply pressure to various limbs on the body have been attempted. However, prior attempts at cessation of hemorrhage from the major blood vessels of the body at or below the inguinal area have not been no completely successful, especially if attempted on gross battle-field wounds such as leg amputations due to anti-personnel mines or high velocity bullet percussion wounds to the lower extremities. Quite often, such wounds do not provide a satisfactory compressible site to stop arterial hemorrhages and require occlusion of the abdominal descending aorta to cut-off the blood supply to the wound in order to protect the patient's life.

However, compressing the abdominal descending aorta is a difficult exercise. One of the major obstacles to providing an effective portable abdominal aortic tourniquet is in providing a focused compression force over the targeted area on the abdomen to achieve aorta occlusion. Typically, most tourniquets apply a constricting force around the circumference of a limb or over a broad area to reduce total blood flow through the limb. Such a broad application of force is ineffective to reduce or occlude blood flow through the descending aorta proximal to the bifurcation in the abdomen due to the deep location of the aorta in the body. A strong focused pressure is required to reach the descending aorta and reduce blood flow. Prior inventions fail to show or disclose a technique for focusing a compression force in the abdomen to operate as an abdominal aortic tourniquet.

For example, U.S. Patent Application Publication No. 2007/0191881 A1 (Amisar et al.) shows a tourniquet that includes a pressure source and a selector lever attached to a cam to facilitate manual selection of a designated pressure. This tourniquet is designed to apply pressure around a limb. There is no teaching in the patent that this device would be effectively usable as an abdominal aortic tourniquet. Further, the air bladder is not a directed air bladder that would focus the compression force, but is rounded to wrap around the limb and spread the pressure force over a broad area. Such a broad application of constricting force is unusable if intended to reduce or occlude circulation through the descending aorta for a non-compressible arterial hemorrhage in the abdominal region.

U.S. Pat. No. 5,234,459 (Lee) shows an inflatable balloon for use in a tourniquet, and discloses a manual pump for inflating the balloon. U.S. Pat. No. 6,884,254 (Brooks) shows a tourniquet system that includes a lever assisted clamp means for tightening the strap around a limb. This patent is representative of a large section of the prior art that uses mechanical means, as opposed to pneumatic means, to provide a constricting force around a limb, but which fail to provide the directed compression force required to restrict blood flow through the descending aorta.

More recent devices have gotten closer to providing reliable occlusion, but require a relatively high degree of experience and skill to apply the device to a patient to achieve satisfactory occlusion to the descending aorta. For example, U.S. Pat. No. 9,149,280 (Croushorn) uses a standard quick connect buckle to connect a strap encircling the intended patient and a windlass to tighten the tourniquet prior to inflating an occluding bladder. While effective, the arrangement nevertheless requires relatively precise placement of the bladder over the intended compression area and re-adjustment of the device during inflation to obtain the intended occlusion results. Moreover, the narrow end of the directed air bladder must be guided during inflation to ensure the successful application of pressure to the targeted abdominal area. In a field environment where many types of emergency response personal with varying types of experience and skill are present, successful administration of the device may require successive attempts to achieve aortic occlusion, or if not properly adjusted may only obtain partial aortic occlusion.

The apparatus disclosed in U.S. Pat. Nos. 9,782,182 and 9,351,737 issued to Carmichael also utilizes a combination of a bladder and windlass design to attempt to focus the tip of the bladder into the abdomen to occlude the descending aorta (similarly to Croushorn). However, Carmichael includes a monolithically arranged bladder shape requiring a pocket into which a sealed bladder is inserted, and which provides a protective cover over the sealed bladder once assembled. The design also includes a pair of "wings" depending laterally from the pocket portion to purportedly strengthen and support the bladder against a retaining belt. In one embodiment, Carmichael utilizes a pair of retaining belts affixed to these wings. The Carmichael monolithic bladder arrangement potentially simplifies manufacturing of the bladder by allowing the entire sealed bladder, cover, and wing portions to be made from a single piece of material and welded using a radio frequency welding source. Nevertheless, the Carmichael design, as with Croushorn, does not self-stabilize the tourniquet against a patient to ensure a perfected penetration of the abdomen to cause reliable aortic occlusion.

Therefore, what is needed is a self-stabilizing, portable abdominal aortic tourniquet that can be rapidly applied under field conditions without extensive training or skill by emergency response personnel.

SUMMARY OF THE INVENTION

The invention is a self-stabilizing pneumatic abdominal aortic tourniquet that utilizes a semi-ridge retaining belt, a ratcheting retaining buckle, and an elastic guide cord on the sides of the device and along a lower penetrating edge of a wedge-shaped bladder. A rigid baseplate is supported by the belt having a width identical with the waist belt so that the baseplate provides a stable base for positioning the bladder over a selected area of the patient's abdomen. The air bladder is affixed to the underside of the baseplate, which is initially kept in a deflated condition collapsed against the baseplate, connects with the elastic cord to bias the tip of the wedge or "V" shaped bladder in the middle of the baseplate. One end of a waist strap includes a geared or toothed section that mates with the ratcheting retaining buckle to allow for an adjustable closure of the retaining belt and bladder around a patient. Once the tourniquet is secured onto a patient's abdomen, an integrated air source operatively connected to and in fluid communication with the air bladder causes inflation and penetration of the lower edge of the "V" shaped bladder against the patient's abdomen thereby causing aorta occlusion.

Other features and objects and advantages of the present invention will become apparent from a reading of the following description as well as a study of the appended drawings.

BRIEF DESCRIPTION OF THE DRAWINGS

A tourniquet incorporating the features of the invention is depicted in the attached drawings which form a portion of the disclosure and wherein.

DESCRIPTION OF THE PREFERRED EMBODIMENTS

Figure 1:
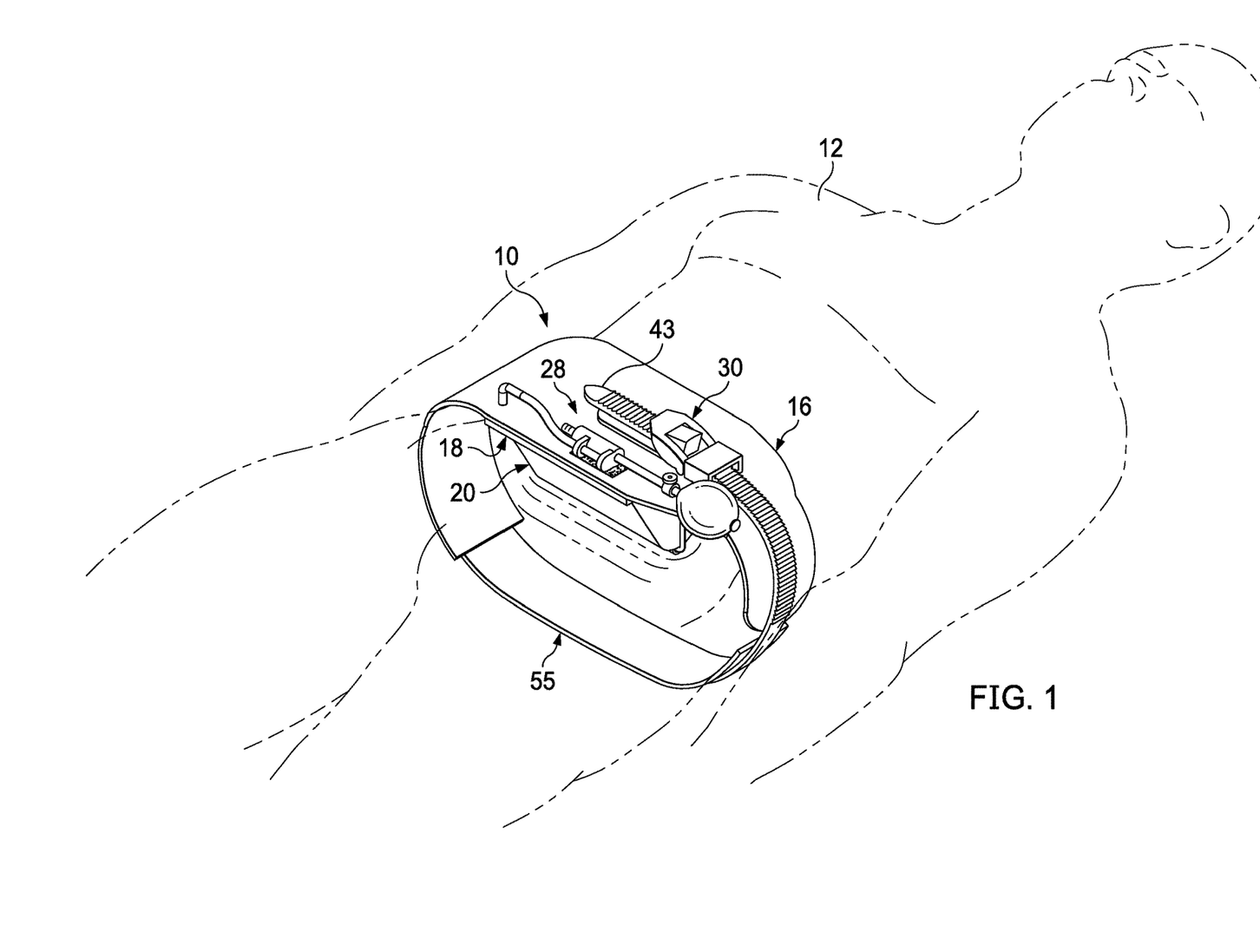
FIG. 1 shows a perspective view of a self-stabilizing pneumatic abdominal aortic tourniquet operatively attached to a patient according to the present invention.
Figure 1A:
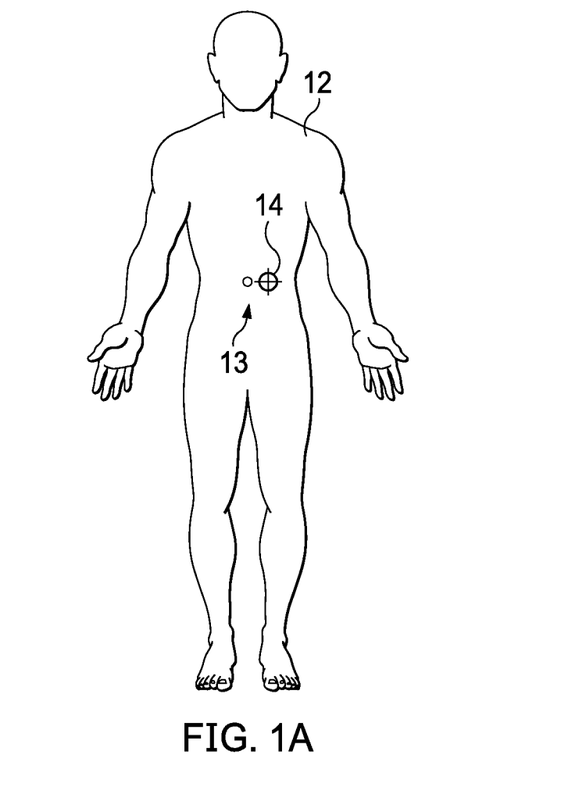
FIG. 1A shows a representative human form indicating where the abdominal aortic tourniquet is to be applied according to the present invention.

Referring to the drawings for a better understanding of the function and structure of the invention, and starting with FIG. 1, a self-stabilizing pneumatic abdominal aortic tourniquet, designated generally as 10, is shown secured around the lower abdomen of a patient 12 for restricting blood flow through the descending aorta proximal to its bifurcation in the lower abdomen to deal with a non-compressible arterial hemorrhage. As shown in FIG. 1A, the tourniquet is arranged over the abdomen to apply localized pressure across a pressure point 14 to restrict blood flow in downstream hemorrhage locations from the point of application over the descending aorta.

Figure 2:
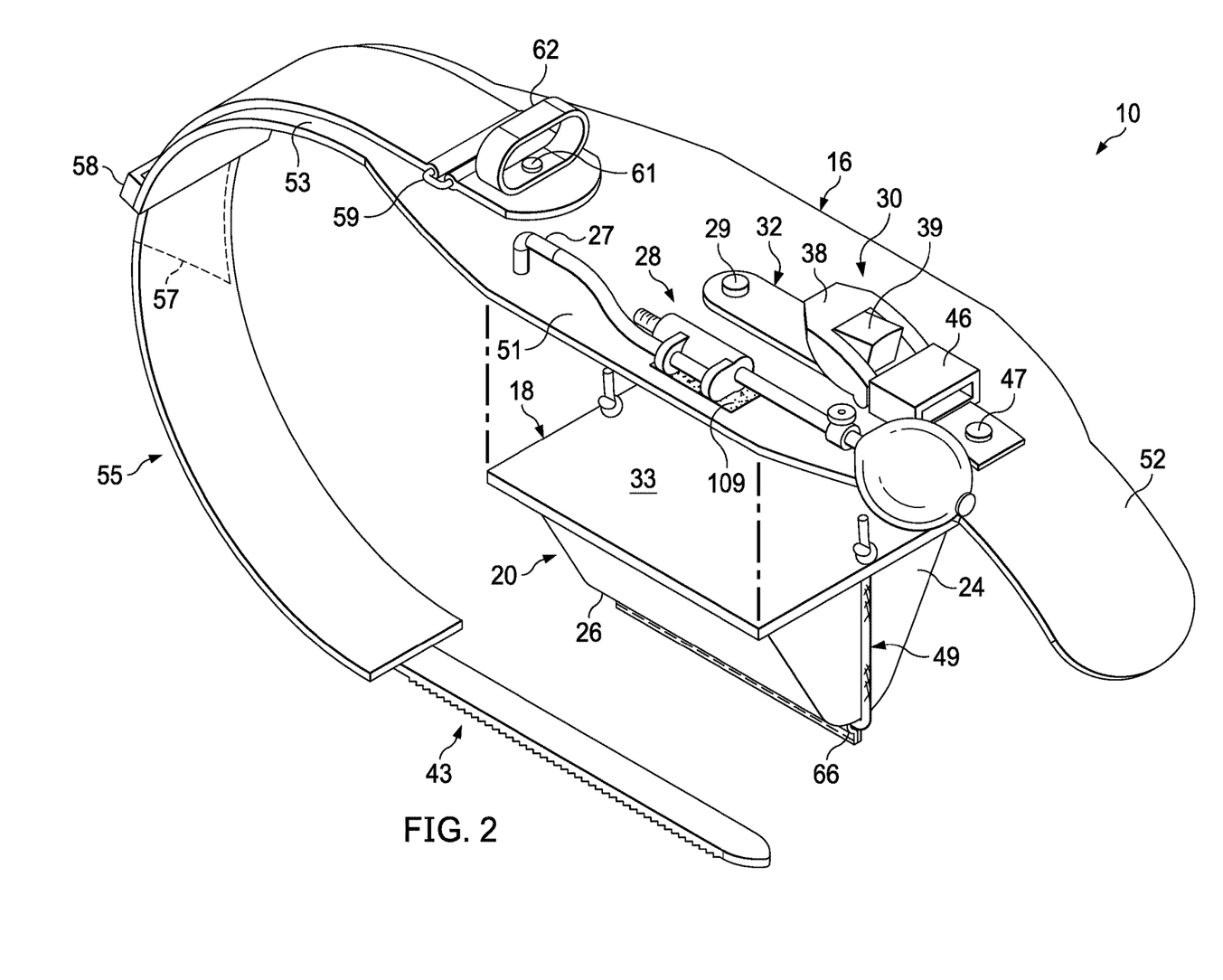
FIG. 2 shows a perspective view of the self-stabilizing pneumatic abdominal aortic tourniquet with the bladder exploded from the baseplate and in an inflated condition.
Figure 3:
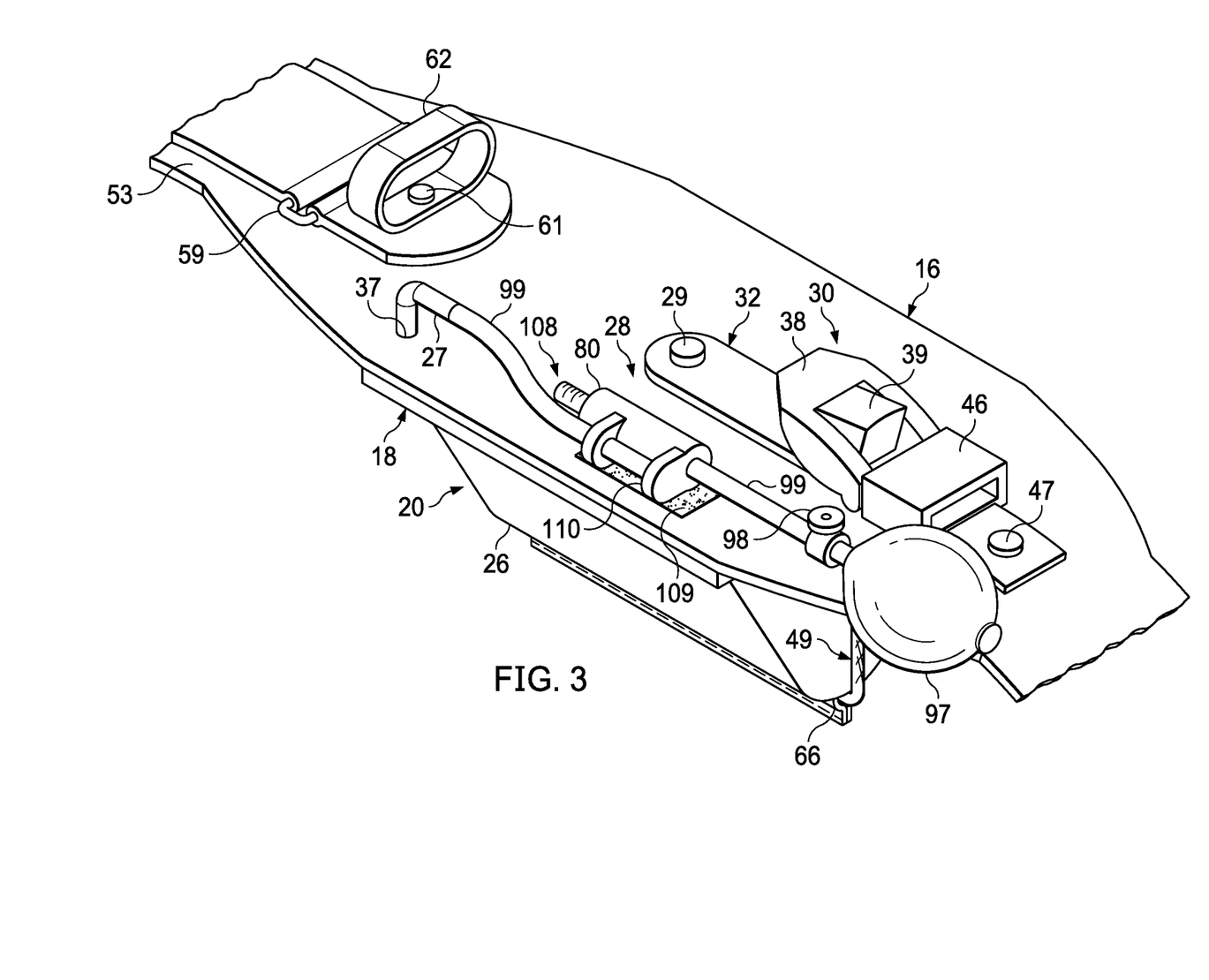
FIG. 3 is an expanded perspective of the aortic tourniquet with a close-up view of its upper part with the bladder affixed to the baseplate in its intended final operational form.
Figure 4:
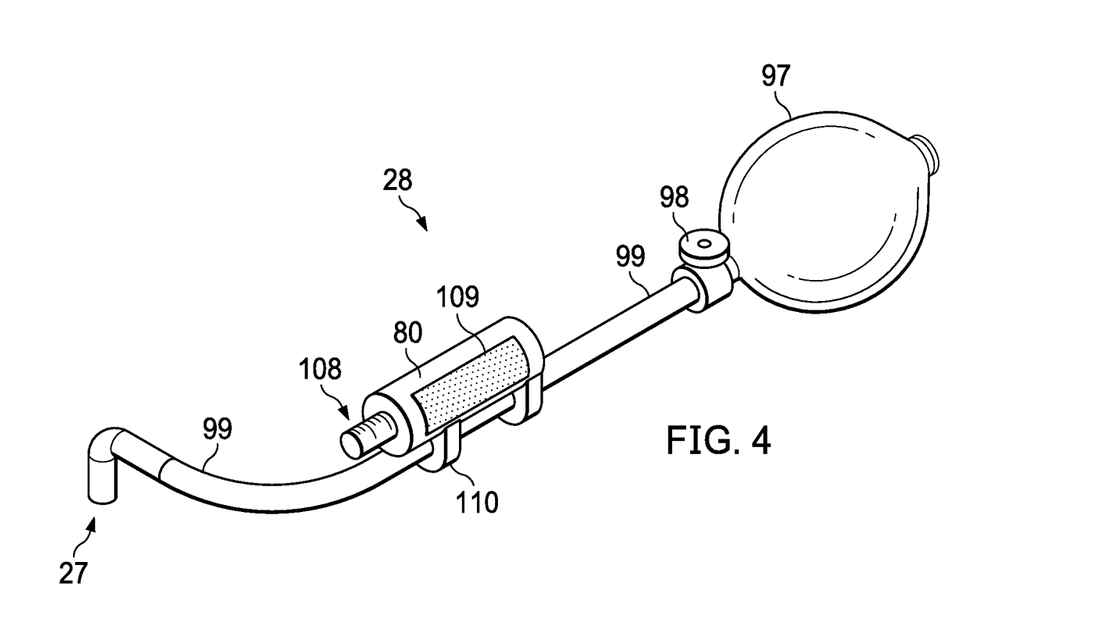
FIG. 4 shows an expanded view of a preferred inflation system of the invention shown in FIG. 1 and shown in FIG. 3.

Referring to FIGS. 2 through 4, the abdominal aortic tourniquet 10 includes an adjustable waist belt 16 for securing the tourniquet around the abdomen of a patient 12. A rigid baseplate 18 is carried on waist belt 16 with the baseplate 18 constructed and arranged to have a width approximately equal to the waist belt 16 so that baseplate 18 extends over the patient's abdomen and especially pressure point 14, and to provide a stable base for positioning the bladder 20 over pressure point 14. Baseplate 18 is preferably made of injected molded rigid plastic material to resist flexing during usage. Baseplate 18 serves two primary purposes: first, it connects the pressure application mechanism—the directed air bladder 20—to waist belt 16; and second, baseplate 18 provides a self-stabilizing platform for anchoring air bladder 20 on the abdomen to prevent pivotal movement during and after inflation As shown in FIG. 2, semi-ridge belt 16 carries directed air bladder 20 on a bottom side 22 of baseplate 18. Belt 16 has a middle portion 51, a long portion 52, and a short portion 53. Baseplate 18 is secured to middle portion 51 via a press stud or rivet 29 and also has its upper surface 33 affixed to the lower surface of belt middle 51 portion with adhesive glue or double-sided adhesive tape (not shown). Belt middle portion 51 also supports ratcheting buckle 30 via a base portion 32 that is secured to the upper surface of portion middle 51 substantially along a longitudinal centerline 31 extending along the length of belt 16. Buckle base 32 has one end secured to press-fit stud 29 located at the center of the middle portion and baseplate, and has its other end affixed to middle portion 51 via another press stud 46 again along center line 31. For securing and releasing belt 16 to patient 12, buckle 30 includes a ratcheting spring loaded, lever arm 38 and a release lever 39. A retaining loop 46 adjacent to press stud 47 secures any loose end of tooth strap portion 46 once tightened around patient 12 as will be explained.

Middle portion 51 also includes an air source 28 for inflating bladder 20. Air source 28 is secured to middle portion 51 via air connector 27 that is operatively connected to bladder 20 and penetrates through baseplate 18 via aperture 37 positioned along the periphery 48 of the baseplate 18. A retaining fastener 109 such as hook and loop tape secures connecting supply tube 99 to middle portion 51 to prevent loose interfering movement during usage.

Semi-rigid belt 16 is preferably made of a polymer substrate of sufficient resiliency to be self-supporting and self-aligning around a patient's abdomen. High density polyethylene (HDPE) sheets having a thickness of at least 1 mm, and cut to conform to the thickness of baseplate 18 are sufficiently resilient for belt 16 to conform to and surround a patient's abdomen while supporting the other operational elements of tourniquet 10. However, semi-ridge belt 16 has a length that only needs to extend over and surround the top and sides of a patient's abdomen. Preferably, belt 16 has one end 52 slightly longer than the other end 53 so that the longer portion 52 supports a waist strap 55 having a thickness substantially similar to the thickness of belt 16, as shown. Each end portion 52,53 of belt 16 while resilient are sufficiently pliable to allow some lateral conformance around the abdomen sides of patient 12 while supporting wide strap 55 surround the underside of the abdomen 13 and under the lumber region of the patient. Strap 55 is anchored to the juncture region of longer portion 52 and middle portion 51 via self-tightening buckle 59 affixed to resilient anchoring material via press stud 61. Stud 61 also fastens a retention loop 59 to the junction region for securing toothed end 43. Preferably, strap 55 is constructed of 90 cm long, nylon webbing and is of sufficient length to go around the patient's torso just above the iliac crest and includes enough slack or extra length to facilitate tightening. This configuration allows for the waist belt 16 and strap 55 to be rapidly fastened around a patient 12 and free end 57 to be pulled to initially tighten the invention against the patient for usage. Free end 57 on strap 55 is angled to facilitate the threading of strap through buckle 59 which permits rapid adjustment to the overall belt length of invention 10 around a patient. Cooperating hook and loop fasteners (not shown) may also be provided for securing a loose end of strap 55 onto itself under distal end 57 once the strap is drawn tight around a patient's abdomen.

Distal end 56 of strap 55 supports a toothed or geared strip 43 on the distal end 36 of the belt 16. Geared strip 43 is configured to be freely inserted into ratcheting buckle 30 in an operative mating relationship such that repeated lifting action of lever arm 38 on buckle 30 causes it to pivot and engage with and move strip 43 through buckle 30 to constrict the diameter of belt 16 surrounding patient 12. Strip 43 also acts as quick connect end to connect belt distal end 36 into buckle 30 via waist strap 55 for quickly attaching and detaching waist strap 55 around the torso. A retaining loop 58 is riveted to the margins of belt portion 52 to secure angled end 57 to strap 55 so that the end 57 does not interfere with the operation of buckle 30.

Referring to FIG. 3, it may be seen that bladder 20 is affixed to under surface of baseplate 16 and depends downward therefrom. Bladder 20 is shown in an inflated state with upper surface 22 of bladder 20 against the underside of the baseplate 18 and the lower, narrow end 26 positioned away from the belt 16 and baseplate 18. As may be seen middle 51 and side portions 52,53 of belt 16 conform in a curved manner to match the contour of the abdomen sides starting at the transition regions of the side portions 52,53 and the middle portion 51. Importantly, baseplate 18 is inflexible and supports middle portion 51 in a rigid relationship to form a stable, flat platform from which bladder 20 may depend downward, thereby allowing for automatic stabilization of bladder upper surface 22 against patient 12 and from which narrow end 26 may uniformly extend during inflation. In order to achieve such uniform extension, mating surfaces of both the bladder 20 to the baseplate 18, and the baseplate 18 to the belt 16 middle portion 51 undersurface must be resiliently bonded along the entire surface areas so that surface movement is prevented during bladder inflation.

Referring to FIG. 4, air source 28 includes hand pump 97 operatively connected to air connector 27 via air supply line 99. Hand bulb pump 97 is of typical construction for blood pressure cuffs, but is preferably of a larger 5 oz capacity to decrease inflation time. Supply line 99 connects the pump 97 to a gauge or monometer 80 having an integrated manifold and cap/clasp 108 at its end proximal to the pump 97. A second clasp 109 aligns supply line 99 along the side of the supply line to a connector 27 on middle section 51 as shown (see FIG. 3). A screw valve 98 is positioned proximal to bulb pump 97 to allow for deflation of bladder 20 and in order to more finely control the pressure applied to patient 12. Screw control valve 98 also allows for the release of air from the bladder 20 when desired such as, for example, when removing the tourniquet 10 in a hospital environment or for manual control of the aortic flow of blood to the lower extremities of a patient while still in the field. As may be understood, endcap 108 is operatively connected to air supply line 99 for adjusting the air pressure within directed air bladder 20 when in an inflated condition 23 or, more importantly, for providing a means to monitor the pressure within the air bladder 20 and automatically releasing pressure within the bladder 20 in over-pressure situations. Monometer 80 is held by line 99 with retaining clips 110 and is fluidly connected to supply line air via connecting cap 108. As may also be understood, monometer provides feedback to an emergency medical practitioner to monitor the air pressure inside bladder 20, and thereby the force directed along its shaped lower edge 26. In addition, monometer may be configured to automatically release air pressure upon reaching a predetermined upper limit of pressure to avoid tissue or internal organ damage to a patient during usage.

Figure 5A:
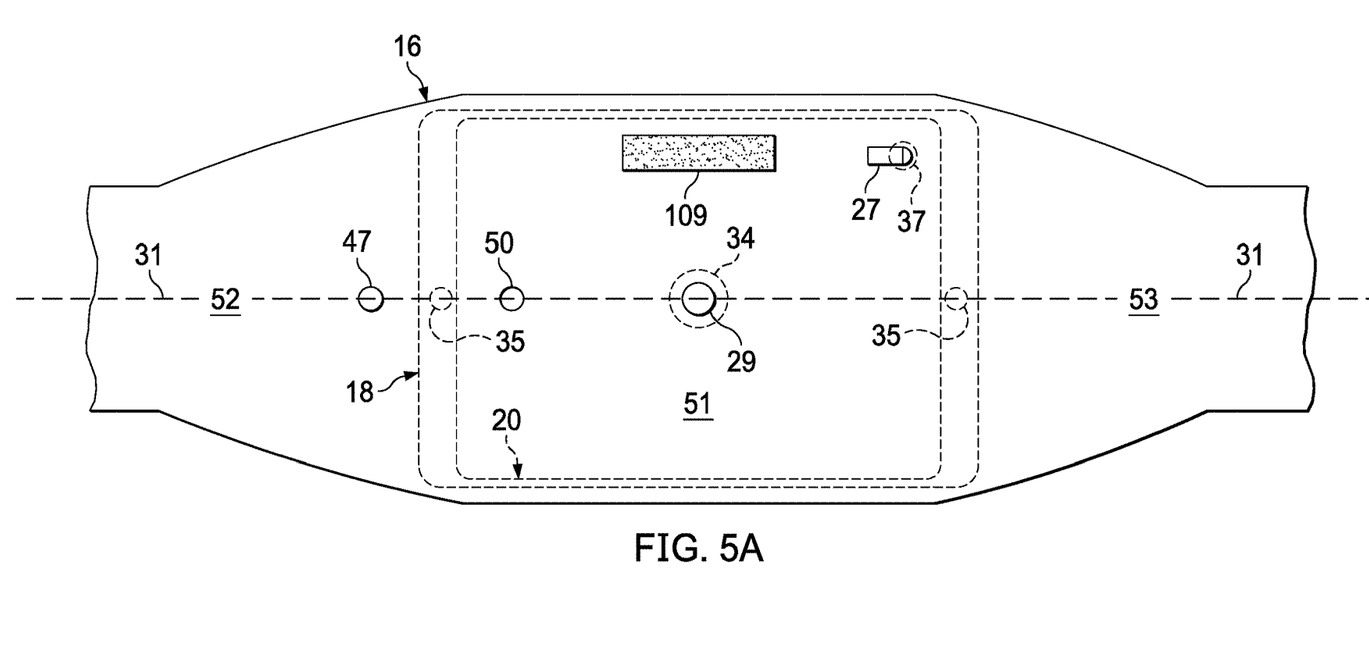
FIG. 5A shows a top plan view of the abdominal tourniquet with the bladder and baseplate shown in phantom according to the present invention.
Figure 5B:
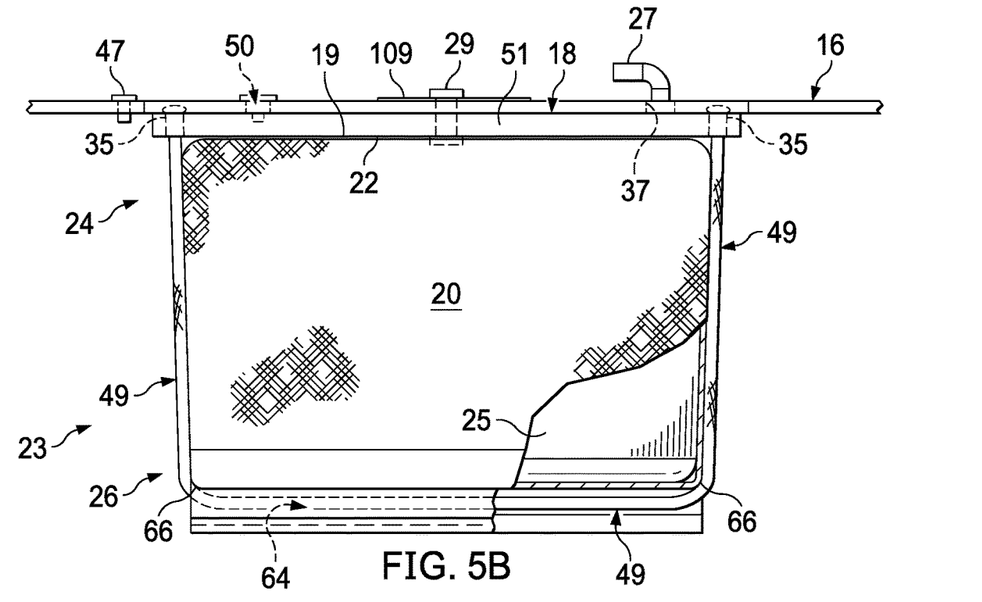
FIG. 5B shows a front elevation view and cut-away of the baseplate carrying the inflatable air bladder and an elastic guide cord positioned along the periphery of the bladder.
Figure 5C:
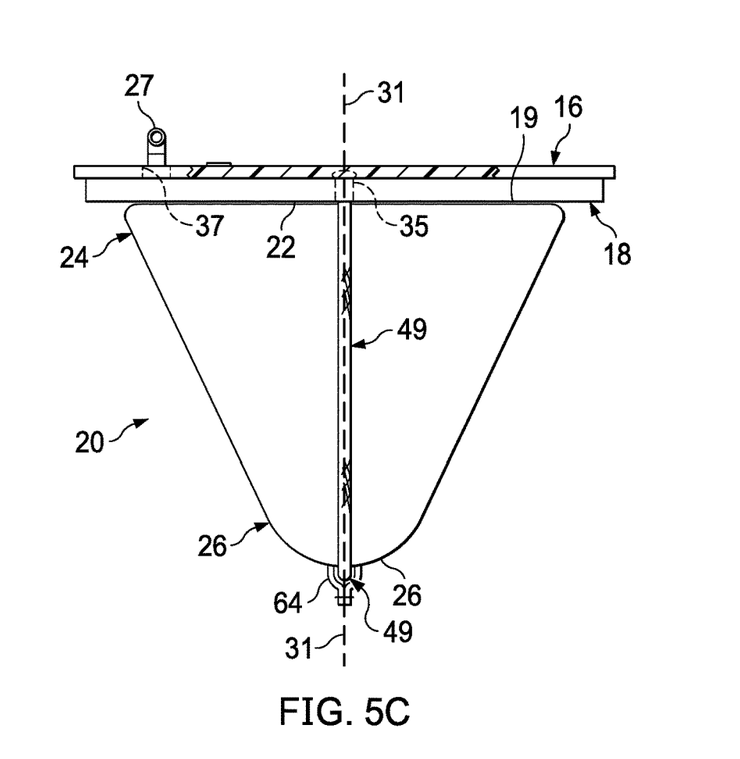
FIG. 5C shows a side elevation view of the baseplate carrying the inflatable air and the elastic guide cord positioned along a centerline bisecting the bladder and positioned within the lower edge of the bladder according to the present invention.

Referring to FIGS. 5A-5C, middle portion 51 of belt 16 includes press-fit stud 29 that also secures baseplate 18 to belt 16 in addition to the adhesive cementing the under surface middle portion 51 to the lower surface 19 of baseplate 18. A second aperture 50 is formed in middle portion 51 to accommodate an additional press-fit stud that secures the middle of ratcheting buckle base 32 to middle portion surface 51. A third press-fit stud 47 secures the distal end of buckle base 32 as already described. Air connector 27 is positioned in the corner of middle portion 51 and fluidly connects with bladder interior 25 through an aperture 37 formed in baseplate 18.

Baseplate 18 includes two apertures 35 along center line 31 at the periphery of baseplate 18. Each aperture 35 acts as an anchor point for the ends of an elastic cord 49 that surround bladder 20. A knot formed in the ends of cord 49 at each aperture 35 secures the ends of cord 49 so that it may be threaded through aperture 35 and positioned downward along a center line of the sides of bladder 20.

As shown in FIG. 5B, bladder 20 is shown in an inflated state 23 configured to have a "V" or "wedge" shape so that, when inflated, pressure is directed toward lower (narrow) end 26 while maintaining cord 49 running down its sides and along the lower end 26. Cord 49 is kept along the center line of the sides of bladder 20 by threading it through a fabric passageway 64 at the lower (narrow) end 26 of bladder 20. Passageway 64 is formed by gathering excess bladder material during manufacturing outside of the sealed extremity of bladder 20 along the lower end 26 and sewing or sealing the extra material a sufficient distance away from the sealed extremity of the lower end 26 of bladder 20 to form a hem wide enough to accommodate the width of the elastic cord 49. Critically, the hem or passageway 64 must at least retain cord 49 at the end points 66 of the narrow end 26 at the juncture of the sidewalls of bladder 20 and preferably run along the entire lower or narrow end 26 of bladder 20 as shown. As will be further explained, positioning the elastic cord at these end points 66 and preferably along the entire edge of the narrow end 26 self-orients the bladder 20 during inflation to ensure targeted application of pressure to the abdomen.

As may be more easily seen in FIG. 5C, width of baseplate 18 is co-extensive with the width of the middle portion 51 of belt 16, thereby providing a self-stabilizing platform for bladder 20. Also, because the length of bladder 20 along center line 31 is longer than the width of middle portion 51, the pressure of the belt 16 when secured around a patient 12 tends to bias the bladder orientation along center line 31, thereby self-orienting lower edge 26 along center line 31 which assists in alignment of directed pressure from bladder 20 to targeted area 14.

Figure 6:
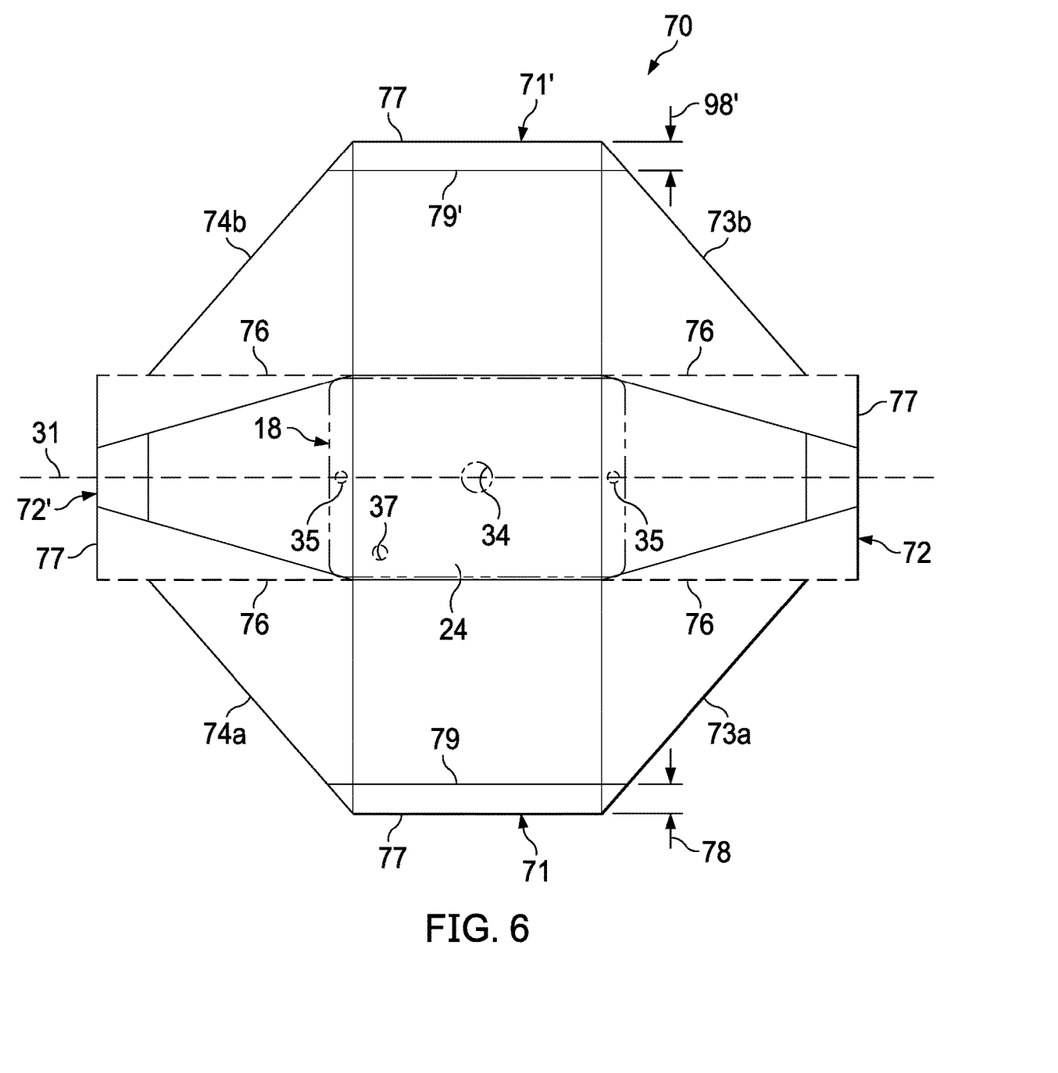
FIG. 6 shows a suitable bladder design pattern implemented in a single, unitary piece of material prior to cutting and fabrication.

Referring now to FIG. 6, an embodiment is shown of a suitable unitary design pattern 70 for fabricating bladder 20 from a single piece of material. Unitary bladder material may be made from various air imperious, pliable materials such as for example rubber and synthetic elastomer composites having limited expansion characteristics, reinforced flexible air impervious composites, and film and coated fabrics, such as nitrile, urethane, vinyl, neoprene and fluoropolymers. Portions 71,71' form front and back side walls of bladder 20, and portions 72,72' form right and left side walls of bladder 20. These sidewalls surround and define upper end 24 of bladder 20 to form a rectangular shape that holds plate 18 which is shown in superimposed phantom lines for mating later on with adhesive. Edges 77 of sidewalls 71,71' are folded together along fold lines as shown so that edges 77 converge to form lower edge 26 and are fused together in an air impervious manner to form a seal edge 79,79' so that the edge is airtight, and an extra amount of material is provided outside of the seal edge 79,79' to create a hem distance 78 between the seal edge 79,79' and edge 77 to create passageway 64 to accommodate elastic cord 49 as previously described. Similarly, separation of unitary design 70 along cut lines 76 form right and left side walls 72,72' that are folded together so that their lower edges 77 meet and be sealed together as with walls 71,71'. Triangular panels 73a,b and 74a,b are folded inward toward center line 31 to facilitate fusing of panels 71,71' with panels 72,72' along their side edges and trimmed appropriately after fusing. As is understood, all edges of panels 71,71' and 72,72' are fused together such that a fluidly sealed interior 25 of air bladder 20 is formed. For example, radio frequency beam welding or thermal fusion sealing techniques are well known in the industry and are suitable for sealing the aforementioned edges. Hem (passageway) 64 having a diameter 78 may be formed with conventional stitching since passageway 64 does not need to be fluidly sealed but only mechanically sealed at lower edge 77.

The tourniquet of the present invention is intended for use in field trauma situations in and under extreme conditions. In such environments, timing is of the utmost importance and mere seconds can determine whether a wounded individual survives. As a result, rapid deployment of the tourniquet 10 is critical and the disclosed embodiment includes features for rapidly securing the tourniquet and expanding the bladder to a desired pressure, thereby achieving occlusion of the descending aorta in a short span of seconds.

Figure 7A:
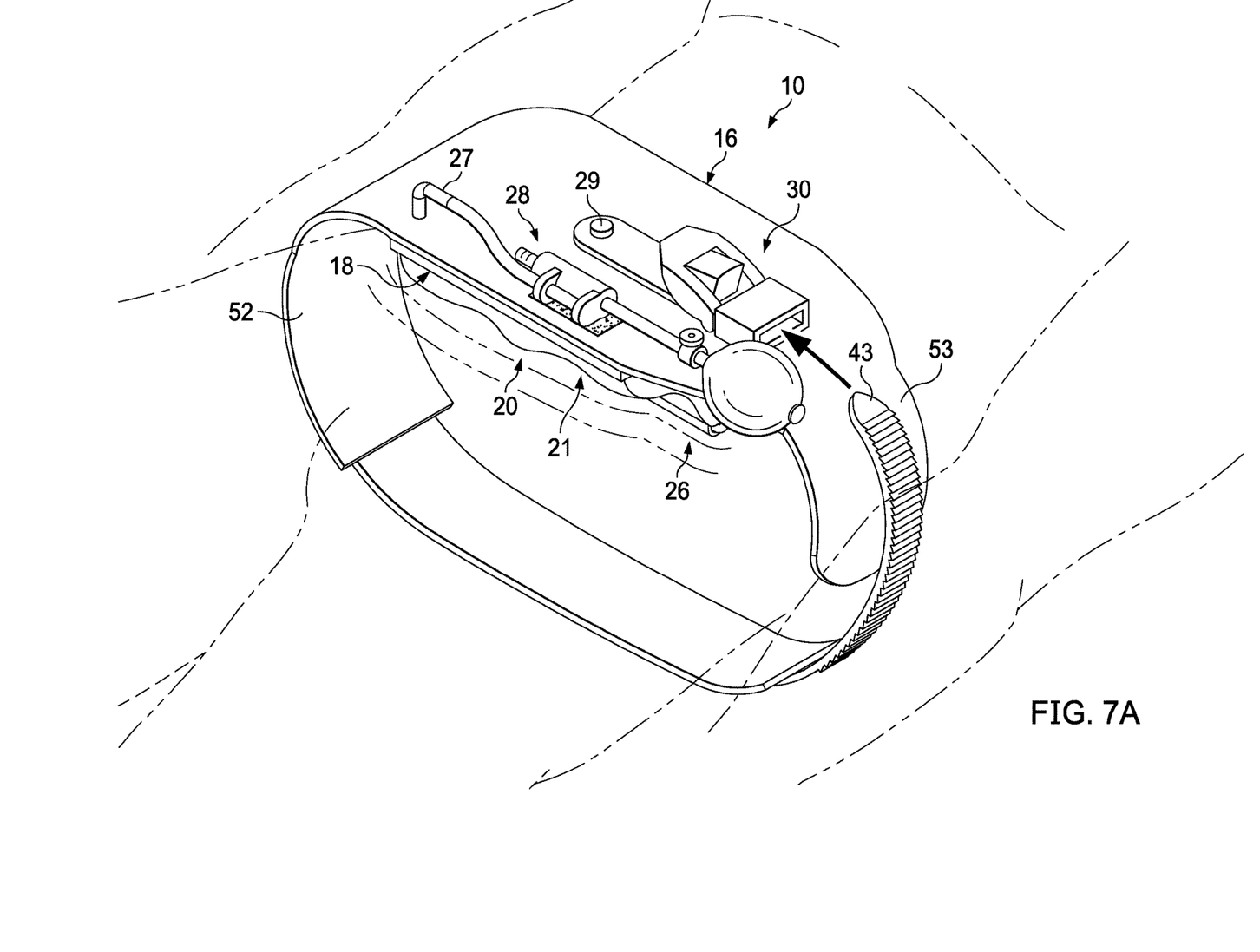
FIG. 7A shows the invention being positioned around a patient's abdomen with the toothed end of the retaining belt about to be inserted into the ratcheting buckle.
Figure 7B:
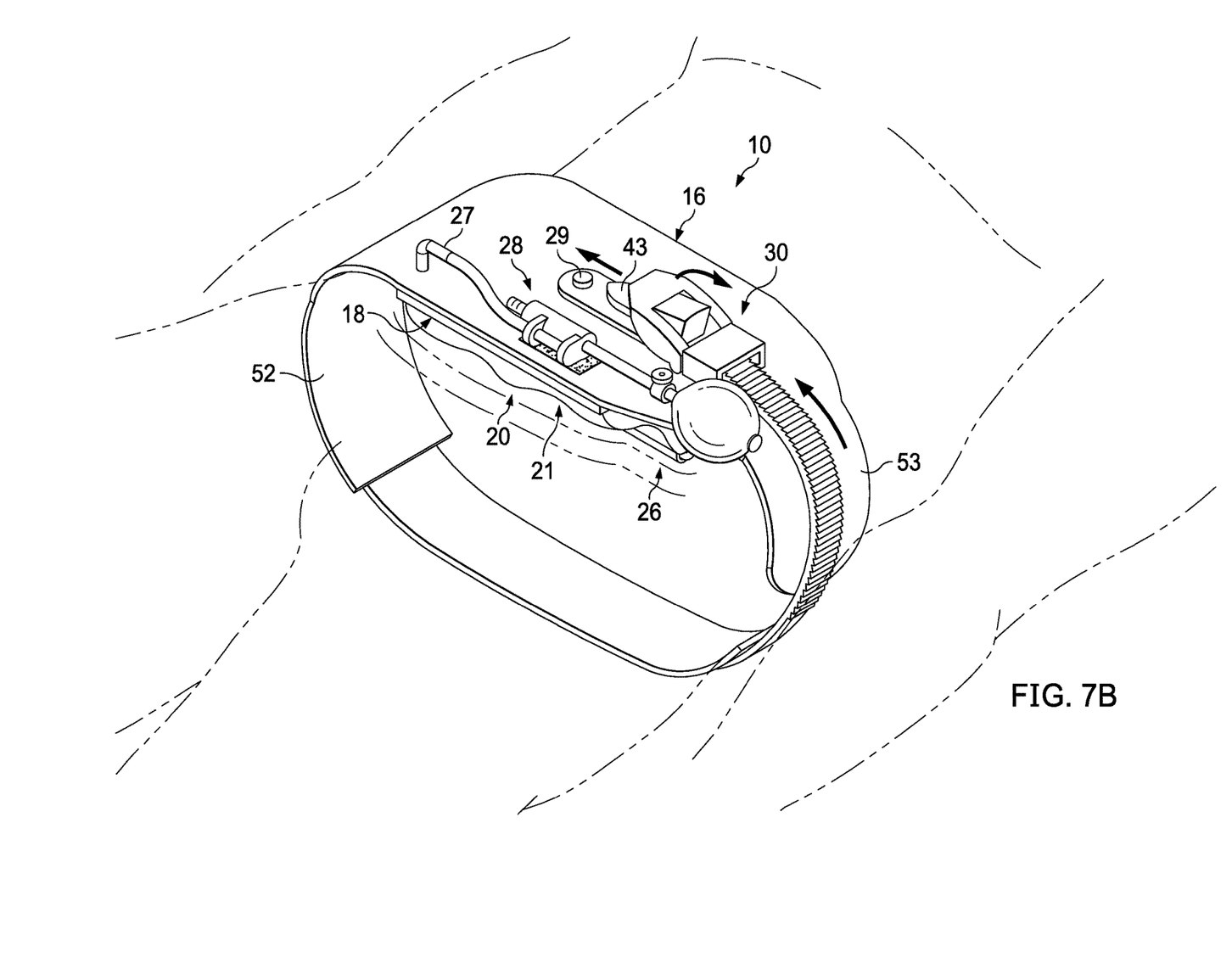
FIG. 7B shows the invention in FIG. 7A with the retaining belt having been tightened around the patient in an uninflated state in preparation for bladder inflation; and, FIG. 7C shows the invention in FIGS. 7A and 7B fully secured onto the patient and the pneumatic bladder in an inflated state and asserting penetrating pressure on the exterior of a patient's abdomen.
Figure 7C:
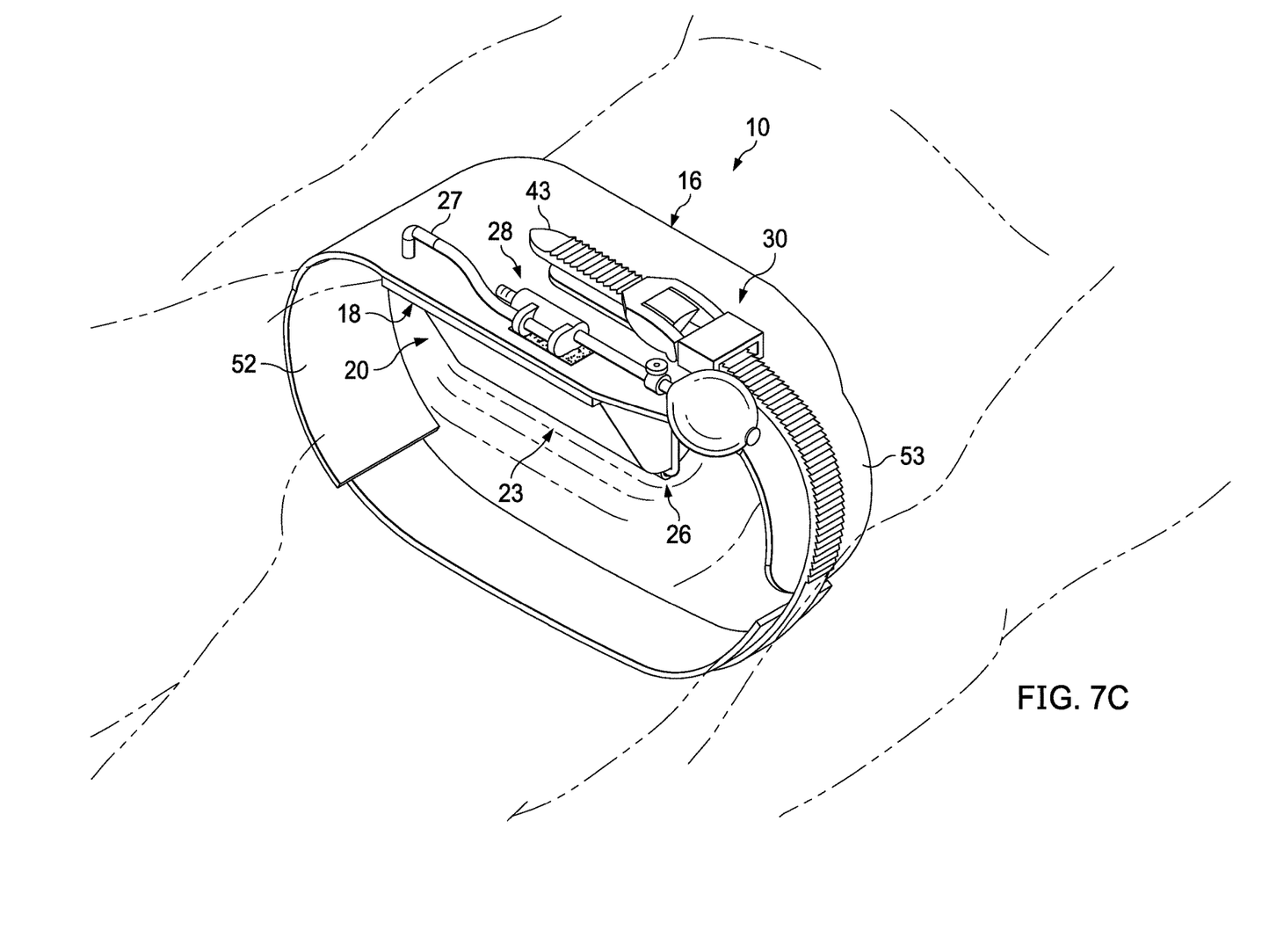

Referring to FIGS. 7A-7C, it may be seen the manner of usage of the invention 10 to rapidly incorporate and use the apparatus on a patient. With air bladder 20 in a deflated condition 21 (FIG. 7A), waist belt 16 is fed around the patient's body 12 with belt 16 lying above the iliac crest. Toothed end 43 of the strap 16 is directed around the patient's abdomen and inserted into ratcheting buckle 30 with baseplate 18 positioned just right of patient body coronal plane, but aligned with target 14 such that the apex (lower edge 26) of the bladder 20 extends across pressure point 14 (see FIG. 1A). The slack is then removed from waist strap 55 by pulling end 57 and any extra strap portion and secure it onto itself using retaining loop 58 and hook and loop connectors on its underside (not shown). Slack may also be removed by simply pushing toothed end 43 through ratcheting buckle 30 as long as enough toothed section of end 43 is retained to allow for ratcheting compression for adjustment during use as will be discussed.

As shown in FIG. 7B, ratcheting buckle 30 is operated by lifting lever arm 38 to engage toothed gearing on end 43. With successive lifting cycles, arm 38 draws end 43 into buckle 30 thereby tightening waist strap 55 around the abdomen 13 of patient 12 and drawing belt 16 and baseplate 18 down, against the abdomen 13 surface. At this stage, bladder 20 is still in a deflated state, designated generally as 21, and is compressed against baseplate 18 due to pressure from the patient's abdomen 13. Importantly, elastic cord 49 holds lower end edge 77 along midline 31 in this deflated state due to the elasticity of cord 49, who's length and elastomeric properties are sized accordingly. Thus, in accordance with FIG. 7B, invention 10 is in a secured state around patient 12, but not yet pneumatically activated to apply pressure to the patient's aorta.

Referring now to FIG. 7C, air bulb 97 is compressed and released repeatedly by an emergency medical practitioner administering the invention 10 to inflate bladder 20. Screw control valve 98 is closed so that air is forced along line 99 and into bladder 20. As air is forced into bladder 20, bladder 20 inflates generally to slightly lift baseplate 18 from abdomen 12, but which is held down by belt 16. As more air is forced into the bladder, lower (narrow) edge 26 is directed downward due to the "V" shape of the bladder to apply focused pressure along its edge 26. Importantly, during inflation elastic cord continues to hold edge 26 in parallel alignment with midline 31 due to elastic forces and the positioning of the hem 64 and apertures 35 (see FIGS. 5A-5C) along this midline 31. Pressure relief valve and gauge indicator 80 (monometer) may be operated to fine tune the application of force by directed air bladder 20 and to warn if a high-pressure condition exists in the bladder, or if pressure falls unacceptably, and to also automatically release air pressure if the pressure inside bladder 20 exceeds a pre-set limit. It will be noted that while a manual bulb pump is shown, the inventors anticipate that an automatic air pressure source such as a $CO_2$ cartridge may be utilized as already taught by Croushorn in U.S. Pat. No. 9,149,280, FIGS. 5A-5B, and his associated description, all of which is hereby incorporated by reference. Further, while not shown, guide markers may be applied to belt 16 and especially to middle section 51 in order to assist with orienting baseplate 18 over the targeted pressure point 14 on the abdomen. In addition, gauge 80 may include indicia along its gauge column to show pressure readings as the gauge column extends outward at its end, as is known.

Generally, the bladder is inflated until the desired effect of cessation of bleeding occurs, or alternatively the desired effect of preload pressure return to the heart is achieved. In particular, narrow end 26 of the directed air bladder 20 presses against the abdomen at target point 14 when the bladder is in an inflated condition, designated generally as 23, so that a constricting force caused by inflation of the directed air bladder 20 against the abdomen is focused against a narrow, elongated defined area to compress the patient's abdominal cavity and restrict blood flow through the abdominal aorta. As may be understood, ratcheting buckle 30 may be actuated to either increase pressure through successive lifting of arm 38, or release pressure by actuating release lever 39. At any point, such as when the device 10 needs to be adjusted or ejected, control value 98 may be opened to allow air to escape from bladder 20 via supply line 99, thereby reducing the pressure within bladder 20. For removal of device 10, release lever 39 may be lifted to allow withdrawal of end 43 from buckle 30 and rapid and easy removal of the invention 10 from around the patient.

While I have shown my invention in one form, it will be obvious to those skilled in the art that it is not so limited but is susceptible of various changes and modifications without departing from the spirit thereof. For example, tourniquet can be repositioned to occlude axial blood vessels in the abdomen leading to the arms, or blood vessels into the neck.

The device may be lowered to surround the inguinal area of the body to occlude blood vessels in that area, or further, a re-sized version of the tourniquet might be utilized on a thigh or leg portion, or an arm portion to effect homeostasis in blood vessels in those areas. In all cases, however, occlusion of a targeted blood vessel achieves cessation of hemorrhage in an injury site different from the point of blood vessel occlusion.

It will also be seen that the tourniquet may be utilized to restrict blood flow at a downstream location rather than total cessation of blood flow, or for other therapeutic purposes. For example, the device may be utilized to restrict blood flow through the aorta in order to "reduce" blood flow to lower the extremities during various medical procedures, and occlusion of the aorta may be utilized in order to prevent blood from leaving the patient's core to elevate the patient's blood pressure in order to enhance CPR.

Having set forth the nature of the invention, what is claimed is:

1. A self-stabilizing method for applying a tourniquet to an abdominal region of a human patient to constrict an aorta of said patient, comprising the steps of:
   a. providing an abdominal tourniquet comprising:
      i. a semi-rigid waist belt adapted to be positioned over a top portion of said abdominal region, said belt having two ends and a middle section between each end configured to cover substantially all of said top portion of said abdominal region, a centerline bisecting said belt longitudinally along the center of its length, said waist belt including a waist strap connecting said ends of said belt for adjustably securing said belt around said abdominal region;
      ii. a rigid rectangular baseplate affixed to an underside of said middle section of said waist belt and having its long side length aligned parallel with said belt centerline and said centerline intersecting the center of said baseplate, wherein said baseplate has a width substantially equal with the width of said waist belt;
      iii. an air bladder having a rectangular base carried on a bottom side of said baseplate with a long side length of said bladder aligned with said belt centerline, wherein said bladder has a deflated condition when said air bladder is collapsed against said baseplate, and has an inflated condition when said air bladder is expanded to extend outwardly from said bottom side of said baseplate;
      iv. said air bladder having a generally elongated "V" shaped construction so that said rectangular based is a wide end of said air bladder carried on said bottom side of said baseplate and an elongated narrow converging end of said air bladder forms an elongated edge positioned away from and parallel to said centerline of said waist belt;
      v. an air source operatively connected to and in fluid communication with said air bladder for operating said air bladder between said deflated condition and said inflated condition;
      vi. a ratcheting buckle affixed to said waist belt for adjustably connecting said waist strap to said waist belt middle section; and
      vii. an elastic retention means connecting said baseplate to said narrow converging end of said air bladder for holding said narrow converging end in parallel relation to said centerline of said waist belt when operating said air bladder from said deflated condition to said inflated condition;
   b. securing said waist strap around said abdomen of said patient by threading a toothed end of said waist strap through said ratcheting buckle and tightening said waist strap, wherein said air bladder is in contact with the surface of said abdomen and positioned over the aorta at or above an umbilical region of said patient;
   c. inflating said air bladder with said air source while said retention means holds said narrow converging end of said air bladder in parallel relation with said centerline of said waist belt;
   d. selectively actuating said buckle to tighten said waist belt against said abdomen; and,
   e. wherein cooperative action between said inflation step and said buckle actuation step causes said narrow edge converging end of said air bladder to apply a constricting force against said abdomen such that said aorta is compressed to occlusion.

2. The method of claim 1, wherein said elastic means connects said narrow converging end of said bladder to said baseplate and said inflation step further includes the step of holding said narrow converging end of said bladder in vertical parallel alignment with said center line of said waist belt and under said middle section during said inflation step.

3. The method of claim 2, further including a bladder manufacturing process comprising the steps of:
   a. cutting a unitary bladder design from a single piece of air-impervious material;
   b. wherein said single unitary piece of air-impervious material includes fold lines that define a rectangular base portion shaped and sized to match the shape of said baseplate;
   c. making four cutting lines in said single piece of air-impervious material oriented to be in parallel relation with said belt centerline and forming two upstanding end walls in said bladder forming two sides to said base portion;
   d. folding two side panels upwards from said base portion and folding up said two upstanding end walls from said base portion upwards to form said narrow converging end of said bladder; and,
   e. welding the upward edges of said upstanding end walls and said upstanding said side panels together to form said bladder from said single piece of air-impervious material in an airtight manner.

4. The method of claim 3, further including the step of sizing said two upstanding side panels to form a hem on the exterior of said welded upward edge of said upstanding side panels, and stitching together a distal edge of said hem spaced from said prior welded seam in said upstanding side panels to form a passageway sized to receive said elastic retention means within said hem and along said narrow converging end of said air bladder.

5. The method of claim 1, wherein said abdominal tourniquet includes an air regulator and said inflation step further includes the step of monitoring and selectively releasing air from said air bladder during said inflation step.

6. The method of claim 5, wherein said step of inflating said air bladder causes hemostasis at a location different than said aorta occlusion location resulting from said aorta occlusion.

7. A self-stabilizing tourniquet for an abdominal region of a human patient, comprising:
   a. a semi-rigid waist belt adapted to be positioned over a top portion of said abdominal region, said belt having two ends and a middle section between each end configured to cover substantially all of said top portion of said abdominal region, a centerline bisecting said belt longitudinally along the center of its length, said waist belt including a waist strap connecting said ends of said belt for adjustably securing said belt around said abdominal region;
b. a rigid rectangular baseplate affixed to an underside of said middle section of said waist belt and having its long side length aligned parallel with said belt centerline and wherein said centerline intersects the center of said baseplate, wherein said baseplate has a width substantially equal with the width of said waist belt;
c. an air bladder having a rectangular base carried on a bottom side of said baseplate with a long side length of said bladder aligned with said belt centerline, wherein said bladder has a deflated condition when said air bladder is collapsed against said baseplate, and has an inflated condition when said air bladder is expanded to extend outwardly from said bottom side of said baseplate;
d. said air bladder having a generally elongated "V" shaped construction so that said rectangular base is a wide end of said air bladder carried on said bottom side of said baseplate and an elongated narrow converging end of said air bladder forms an elongated edge positioned away from and parallel to said centerline of said waist belt;
e. an air source operatively connected to and in fluid communication with said air bladder for operating said air bladder between said deflated condition and said inflated condition;
f. a ratcheting buckle affixed to said waist belt for adjustably connecting said waist strap to said waist belt middle section; and
g. an elastic retention means connecting said baseplate to said narrow converging end of said air bladder for holding said narrow converging end in parallel relation to said centerline of said waist belt when operating said air bladder from said deflated condition to said inflated condition.

8. The self-stabilizing tourniquet as recited in claim 7, further including an air pressure regulator operatively connected to said air source for monitoring pressure in said bladder when filled with pressurized air and for selectively releasing said pressurized air upon reaching an over-pressurized state.

9. The self-stabilizing tourniquet as recited in claim 8, wherein said waist strap includes a geared end for engaging said ratcheting buckle when inserted therein.

10. The self-stabilizing tourniquet as recited in claim 9, wherein said elastic retention means comprises an elastic cord connected to each side of said baseplate along said center line of said waist belt and connected to and threaded along the elongated edge of said narrow end of said bladder such that said narrow converging end is biased toward said baseplate.

11. The self-stabilizing tourniquet as recited in claim 10, wherein said bladder comprises a single unitary piece of air-impervious material.

12. The self-stabilizing tourniquet as recited in claim 10, wherein said bladder comprises:
a. a single unitary piece of air impermeable material adapted to be folded into said bladder;
b. wherein said single unitary piece of air impermeable material includes fold lines that define a rectangular base portion shaped to conform to the shape and size of said baseplate;
c. wherein said single unitary piece of air impermeable material includes four cut lines, wherein said cut lines define two upstanding end panels having one end forming two opposing sides of said rectangular base portion and adaptable for positioning said end panels in orthogonal relation to said belt center line;
d. wherein said fold lines of said single unitary piece of air impermeable material further define two upstanding side panels having one side defining opposing two sides of said rectangular base portion;
e. wherein said two side panels and said two end panels are folded together at their upper edges to form said elongated edge of said bladder so that said narrow converging end of said bladder is positioned in parallel relation to said belt center line when said bladder is in an inflated state; and,
f. wherein said upper edges of said end and side panels are welded together to form said air bladder.

13. The self-stabilizing tourniquet as recited in claim 12, wherein said single unitary piece of air impermeable material further includes a hem extending away from said upper edge of said upstanding side panels and sized to hold said elastic retention means along said elongated edge of said bladder.

14. The self-stabilizing tourniquet as recited in claim 13, wherein said air source comprises a hand bulb pump and an airline affixed to said middle section of said waist belt and fluidly connecting said pump to said air bladder through said baseplate.

15. The self-stabilizing tourniquet as recited in claim 14, wherein said waist belt is comprised of high-density polyethylene sheet.

16. The self-stabilizing tourniquet as recited in claim 14, wherein said hem of said single unitary piece of air impermeable material adapted to hold said elastic retention means along said elongated edge of said bladder.

17. The self-stabilizing tourniquet as recited in claim 7, wherein said bladder comprises:
a. a single unitary piece of air impermeable material adapted to be folded into said bladder;
b. wherein said single unitary piece of air impermeable material includes fold lines that define a rectangular base portion shaped to conform to the shape and size of said baseplate;
c. wherein said single unitary piece of air impermeable material includes four cut lines, wherein said cut lines define two upstanding end panels having one end forming two opposing sides of said rectangular base portion and adaptable for positioning said end panels in orthogonal relation to said belt center line;
d. wherein said fold lines of said single unitary piece of air impermeable material define two upstanding side panels having one side defining two opposing sides of said rectangular base portion;
e. wherein said two side panels and said two end panels are folded together at their upper edges to form said elongated edge of said bladder so that said narrow converging end of said bladder is positioned in parallel relation to said belt center line when said bladder is in an inflated state; and,
f. wherein said upper edges of said end and side panels are welded together to form said air bladder.

18. A self-stabilizing tourniquet for application to an abdominal region of a human patient for the constricting of an aorta of said patient, comprising:
a. means for holding said tourniquet over said abdominal region in a semi-rigid state that resists twisting, said holding means adapted to be positioned over a top portion of said abdominal region, said holding means including two ends and a middle section between each end, a centerline bisecting said holding means longitudinally along the center of its length, and said holding means including means for connecting said ends of said holding means around the underside of said abdominal region;

b. a baseplate affixed to said holding means;

c. an air bladder supported by said baseplate and expandable downward from a bottom side of said baseplate, wherein said air bladder has a generally elongated "V" shape so that a wide end of said air bladder generally bears against said baseplate and an elongated narrow converging end of said air bladder forms an elongated edge positioned away from and parallel to said centerline of said holding means;

d. wherein said air bladder is formed from a unitary piece of air impermeable material having fold lines that define a rectangular base portion, two upstanding side panels extending from two opposing sides of said base portion, and two upstanding end panels extending from the two other sides of said base portion, wherein the upward edges of said side and end panels are fused together to form said narrow converging end of said bladder;

e. an air source operatively connected to and in fluid communication with said air bladder for operating said air bladder between a deflated condition and an inflated condition;

f. said connecting means including a geared end tip and said holding means including tensioning means configured to accept said geared end tip and operatively movable to draw in said geared end tip to compress said holding means against said patient; and g. an elastic retention means connecting said baseplate to said narrow converging end of said air bladder for holding said narrow converging end of said bladder in parallel relation to said centerline of said holding means when operating said air bladder from said deflated condition to said inflated condition.

19. The self-stabilizing tourniquet as recited in claim 16, wherein said unitary piece of air impermeable material further includes a hem extending away from said upward edge of said upstanding side panels and sized to thread said elastic retention means within said hem and along said narrow converging end of said bladder.

20. The self-stabilizing tourniquet as recited in claim 19, wherein said elastic retention means comprises an elastic cord connected to each side of said baseplate along said center line of said holding means and connected to and threaded along the elongated edge of said narrow converging end of said bladder such that said narrow converging end is biased toward said baseplate.

* * * * *